US 9,999,781 B2

(12) United States Patent
Gale et al.

(10) Patent No.: US 9,999,781 B2
(45) Date of Patent: Jun. 19, 2018

(54) SYSTEM AND METHOD FOR MICROMAGNETIC STIMULATION OF THE PERIPHERAL NERVOUS SYSTEM

(71) Applicant: THE CLEVELAND CLINIC FOUNDATION, Cleveland, OH (US)

(72) Inventors: John T. Gale, Chardon, OH (US); Hyun-Joo Park, North Royalton, OH (US); Matthew Johnson, Chesterland, OH (US); Susan Thompson, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 297 days.

(21) Appl. No.: 14/710,767

(22) Filed: May 13, 2015

(65) Prior Publication Data

US 2015/0328477 A1 Nov. 19, 2015

Related U.S. Application Data

(60) Provisional application No. 61/992,357, filed on May 13, 2014.

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01)

(58) Field of Classification Search
CPC .............................................. A61N 2/00–2/12
See application file for complete search history.

(56) References Cited

U.S. PATENT DOCUMENTS

| 8,690,748 | B1 | 4/2014 | Fu |
| 2008/0319506 | A1 | 12/2008 | Cauller |
| 2009/0254146 | A1 | 10/2009 | Bonmassar et al. |

OTHER PUBLICATIONS

Lee et al., "Activation of Retinal Ganglion Cells by Microcoil-Induced Magnetic Stimulation", May 9, 2012, 3:45 PM-5:30 PM, pp. 1-2. Abstract Only.
Srinivas, "'MagStim': Micromagnetic Neurostimulation for Implantable Systems", Raleigh, North Carolina, 2011, pp. 1-101.
International Search Report and Written Opinion for PCT/US2015/030473, dated Sep. 2, 2015, pp. 1-12.

*Primary Examiner* — Thaddeus Cox
(74) *Attorney, Agent, or Firm* — Tarolli, Sundheim, Covell & Tummino LLP

(57) ABSTRACT

One aspect of the present disclosure relates a system that can employ micromagnetic stimulation to activate and/or suppress conduction in at least a portion of a peripheral nerve. The system can include a stimulator to provide a time-varying stimulus. The system can also include a microcoil that can be operatively coupled to the stimulator to receive the time-varying stimulus. Based on the time-varying stimulus, the microcoil can provide an electromagnetic induction to the peripheral nerve to activate and/or suppress conduction.

13 Claims, 6 Drawing Sheets

SYSTEM AND METHOD FOR MICROMAGNETIC STIMULATION OF THE PERIPHERAL NERVOUS SYSTEM

RELATED APPLICATIONS

This application claims the benefit of U.S. Provisional Application No. 61/992,357, filed May 13, 2014, entitled "SYSTEM AND METHOD FOR MICROMAGNETIC STIMULATION OF THE PERIPHERAL NERVOUS SYSTEM." This provisional application is hereby incorporated by reference in its entirety for all purposes.

TECHNICAL FIELD

The present disclosure relates generally to micromagnetic stimulation of the peripheral nervous system and, more specifically, to systems and methods that can employ one or more microcoils to activate or suppress a peripheral nerve.

BACKGROUND

Generally, peripheral nerve stimulation is a neuromodulation technique in which electrical current is applied to a peripheral nerve. There are many applications of peripheral nerve stimulation, including: vagus stimulation for epilepsy, functional electrical stimulation for spinal cord injury, pudendal nerve stimulation for bladder control, hypoglossal nerve stimulation for sleep apnea, and peroneal nerve stimulation for food drop. Traditionally, electrical stimulation has been used in peripheral nerve stimulation.

Electrical stimulation employs a direct interface between a metal contact of a peripheral nerve electrode and the biological tissue. Depending on the current injected to the tissue through the metal contact, oxidation and reduction ("redox") phenomena can occur at the neural interfaces. These redox phenomena can cause tissue damage and electrode corrosion, which limit the long-term use of electrical stimulation. Therefore, the amount of charge that can be used is strictly restricted for practical use. Additionally, the direct neural interface can act as a heat sink in magnetic resonance imaging (MRI) scanning machines, limiting MRI scanning for patients with implanted peripheral nerve electrodes.

Magnetic stimulation, which stimulates excitable tissue with an electric current induced by a time-varying magnetic field, is advantageous to electrical stimulation because it does not lead to redox phenomena or reduced MRI interference. In magnetic stimulation, there is no direct charge transfer between a metal electrode contact and the biological tissue. Instead, magnetic stimulation induces an electric current by an applied time-varying magnetic field. However, conventional magnetic stimulation requires a large inductor coil (e.g., many centimeters in size) that is not practical for implantation into the body.

SUMMARY

The present disclosure relates generally to micromagnetic stimulation of the peripheral nervous system and, more specifically, to systems and methods that can employ one or more microcoils (e.g., sized on the order of millimeters or less) to activate or suppress a peripheral nerve. The microcoils can alleviate the problems inherent to electrical stimulation (e.g., redox phenomena and MRI interference), while being of a size that can be easily implanted into the body.

In one aspect, the present disclosure can include a system that employs micromagnetic stimulation. The system can include a stimulator to provide a time-varying stimulus. The system can also include a microcoil operatively coupled to the stimulator to receive the time-varying stimulus. The microcoil can provide an electromagnetic induction based on the time-varying stimulus. The electromagnetic induction can activate or suppress the conduction in the peripheral nerve.

In another aspect, the present disclosure can include a method for stimulating a portion of a peripheral nerve of a subject. A time-varying current can be delivered through a microcoil to generate a corresponding time-varying magnetic field in the adjacent excitable tissue. The microcoil can be located outside the epineurium of the peripheral nerve. An electric field gradient can be induced within one or more axons within the portion of the peripheral nerve based on the time-varying magnetic field to stimulate the peripheral nerve.

In a further aspect, the present disclosure can include a method for constructing a neural prosthetic device. The neural prosthetic device can stimulate a portion of a peripheral nerve of a subject. The method can include steps that can include: coating at least a portion of an elastic material with a biologically compatible material; and forming a microcoil of a size less than or equal to 10 millimeters from the coated elastic material. The microcoil can be placed outside the peripheral nerve without penetrating the peripheral nerve to activate or suppress the portion of the peripheral nerve via electromagnetic induction.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
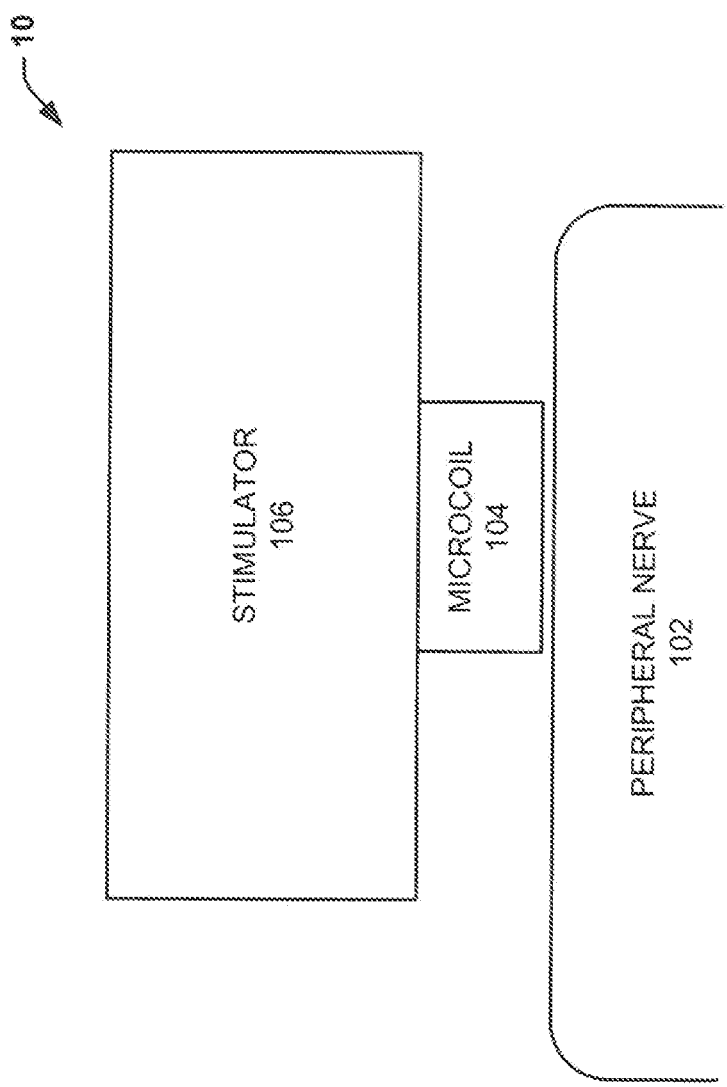
FIG. 1 is a schematic block diagram showing a system that employs micromagnetic stimulation to stimulate a peripheral nerve in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "peripheral nervous system" can a network of motor, sensory, and autonomic nerves that connect the brain and spinal cord to the rest of a patient's body. For example, the peripheral nervous system can control the functions of sensation, movement, and motor coordination.

As used herein, the term "peripheral nerve tissue" can refer to a peripheral nerve (including a plurality of fascicles), a nerve root, a fascicle (housing a group of nerves), and/or a single peripheral nerve. Examples of different peripheral nerves can include: the brachial plexis nerve, the common peroneal nerve, the femoral nerve, the lateral femoral cutaneous nerve, the median nerve, the radial nerve, the sciatic nerve, the spinal accessory nerve, the tibial nerve, and the ulnar nerve.

As used herein, the term "epineurium" can refer to the outermost layer of dense connective tissue surrounding a peripheral nerve. In some instances, the epineurium can surround multiple nerve fascicles, blood vessels that supply the nerve, etc.

As used herein, the term "exposed" can refer to a portion of the peripheral nervous system (e.g., a nerve) that is made accessible for an external device (e.g., a neural prosthesis with one or more microcoils) to be placed in proximity to or in contact with the portion of the peripheral nervous system.

As used herein, the term "neural prosthesis" or "neural-prosthetic" can refer to a device that interfaces with a portion of the peripheral nervous system to supplement and/or replace one or more functions lost as a result of disease or injury. The neural prosthesis can stimulate conduction in the nerve and/or block conduction in the nerve.

As used herein, the term "neurosurgical procedure" can refer to a surgical procedure that relates to implementation of at least a portion of a neural prosthesis (e.g., a chronic neural prosthetic system) within at least a portion of a patient's peripheral nervous system.

As used herein, the term "neural stimulation" can refer to the activation or suppression of one or more nerves through an external source. For example, the external source can activate a nerve by causing the nerve to generate an action potential. In another example, the external source can suppress the nerve by causing the nerve not to generate an action potential.

As used herein, the term "activation" or "activate" can refer causing a nerve to conduct. For example, the conduction can include the generation of an action potential in an axon of the nerve and/or the release of neurotransmitter from the terminal of a nerve. An activated nerve can, in turn, activate one or more other nerves, causing these activated nerves to conduct. As an example, activation of a portion of the peripheral nerve can include the activation of one or more individual nerves within the portion of the peripheral nerve in proximity to a magnetic stimulation and the subsequent activation of additional peripheral nerves.

When used herein, the term "suppression," can refer to inhibiting conduction in a nerve. Suppression can have the opposite effects to activation (e.g., a suppressed portion of the peripheral nerve can stop conducting).

As used herein, the term "magnetic stimulation" can refer to a type of neural stimulation provided by an external device that employs electromagnetic induction to activate one or more nerves.

As used herein, the term "micromagnetic stimulation" can refer to an acute magnetic stimulation that can target a small number of nerves (e.g., for peripheral nerve stimulation) by utilizing inductors (e.g., microcoils) that provide the electromagnetic induction to stimulate the small number of nerves.

As used herein, the term "microcoil" or "microcoil inductor" can refer to an inductor (e.g., of a size less than or equal to 10 millimeters) of a geometry (e.g., a coiled geometry) utilized in micromagnetic stimulation. The microcoil can focus the magnetic fields into a peripheral nerve and allow the generation of an electrical gradient within the peripheral nerve.

As used herein, the term "operatively coupled" can refer to two or more components that are linked so that they perform their associated function cooperatively and/or in combination.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

As used herein, the term "medical professional" can refer to any person involved the conducting a neurosurgical procedure including, but not limited to, physicians, medical students, nurse practitioners, nurses, and other operating room staff.

II. Overview

The present disclosure relates generally to micromagnetic stimulation of the peripheral nervous system and, more specifically, to systems and methods that can employ one or more microcoils to stimulate (e.g., activate or suppress) at least a portion of a peripheral nerve. The micromagnetic stimulation with microcoils can alleviate problems inherent to electrical stimulation (e.g., redox phenomena and MRI interference) while the microcoils are of a size that can be easily implanted into the body.

Traditional magnetic stimulation is advantageous to traditional electrical stimulation, which injects charge into the surrounding tissue between contacts. In magnetic stimulation, current is induced in a peripheral nerve tissue by time varying magnetic fields emanating from an inductor without injecting charge into the tissue. The current in the tissue can be generated due to ion displacement in the tissue with no net charge injected to the tissue, mitigating the deleterious oxidation or reduction phenomenon and the electrode-tissue interface due to injected charge. However, the spatial resolution of traditional magnetic stimulation is poor and requires a large amount of current that can lead to heating and interference.

Micromagnetic stimulation utilizes smaller magnetic coils that have a better spatial resolution than traditional magnetic stimulation and requires a smaller amount of current that does not lead to the problems inherent to traditional magnetic stimulation. In micromagnetic stimulation, microcoil inductors ("microcoils") can be designed with a geometry selected to focus stimulation and located in proximity to or in contact with the surface of the peripheral nerve tissue to focus the magnetic fields into the tissue. Stimulation through the microcoils can allow for the generation of an electrical gradient at a depth within the tissue to activate and/or suppress one or more portions of the peripheral nerve tissue. A current can be generated based on the electrical gradient (e.g., an action potential can be transmitted by an axon of the peripheral nerve if the electrical gradient is above a threshold voltage for conduction).

III. Systems

One aspect of the present disclosure can include systems that can activate and/or suppress conduction in one or more areas of a peripheral nerve with micromagnetic stimulation. Although not wishing to be bound by theory, it is believed that microcoils used in micromagnetic stimulation can focus a magnetic field at a depth into a tissue, allowing for the targeted generation of an electrical gradient at the depth within the tissue to activate one or more axons within the peripheral nerve (e.g., an action potential can be transmitted by an axon of a nerve if the electrical gradient is above a threshold voltage for conduction and the conduction can be transmitted to another nerve via neurotransmitter release).

An example of a system 10 that can employ micromagnetic stimulation to activate and/or suppress a portion of a peripheral nerve 102 is shown in FIG. 1. In some instances, the micromagnetic stimulation can activate a portion of the peripheral nerve 102. In other instances, the micromagnetic stimulation can suppress a portion of the peripheral nerve 102. In still other instances, the micromagnetic stimulation can activate a portion of the peripheral nerve 102, while suppressing another portion of the peripheral nerve.

The system 10 can include components that can facilitate the micromagnetic stimulation, including the microcoil 104 and a stimulator 106 that is electrically coupled to the microcoil. The microcoil 104 can stimulate the portion of the peripheral nerve 102 via electromagnetic induction. The stimulator 106 can provide a time-varying stimulus to the microcoil 104. For example, the time-varying stimulus can be a time-varying current. Based on the time-varying stimulus, the microcoil 104 can generate a time-varying magnetic field. Temporal changes in the magnetic field can induce an electrical field in one or more areas of the peripheral nerve 102 to stimulate the peripheral nerve. For example, the stimulation can activate and/or suppress conduction in the peripheral nerve. The activation can lead to restoration of paralyzed function, while the suppression can lead to the minimization of a pain sensation.

As noted, the micromagnetic stimulation of system 10 is advantageous over traditional electrical stimulation and magnetic stimulation at least because micromagnetic stimulation can generate at least one of conduction and release of neurotransmitter from one or more axons within the portion of the peripheral nerve 102 with high specificity without injecting charge into the peripheral nerve. The micromagnetic stimulation of system 10 can exhibit a higher spatial resolution than traditional magnetic stimulation without causing unfavorable heating (e.g., radio frequency heating in magnetic resonance imaging), electromagnetic interference (e.g., with electronic equipment, etc.) and/or demagnetization (e.g., of ID badges, credit cards, and the like). The micromagnetic stimulation is also favorable to traditional electrical stimulation because no net charge is delivered to the tissue, causing no damaging reduction and/or oxidation reactions in the tissue. Additionally, the microcoils 104 used in micromagnetic stimulation do not puncture the tissue like the contacts used for some traditional electrical stimulation techniques. In fact, the microcoils 104 do not make direct contact with the peripheral nerve 102. Instead, the microcoils 104 are placed external to and/or in contact with the epineurium of the peripheral nerve 102.

Figure 2:
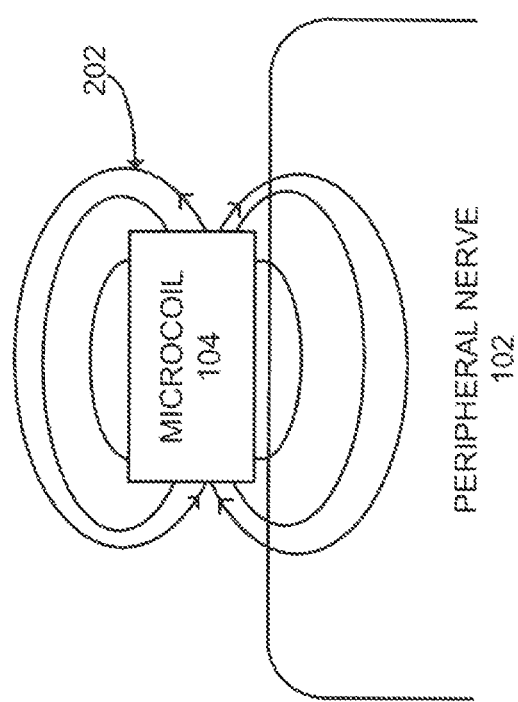
FIG. 2 is a schematic diagram showing the magnetic field produced by the microcoil in the system of FIG. 1.

As shown in FIG. 2, the microcoil 104, which can be placed external to or in contact with the epineurium of the peripheral nerve 102, can emanate a time-varying magnetic field 202 in response to a time-varying electric current delivered to the microcoil (e.g., by stimulator 106 in FIG. 1). The time-varying magnetic field 202 can allow for the generation of an electric field gradient at a depth within the tissue of the portion of the peripheral nerve 102 to induce an activating current flow within one or more nerves within the portion of the peripheral nerve 102. The electric field gradient can change the transmembrane voltages of one or more axons within the peripheral nerve 102 sufficient to activate and/or suppress the peripheral nerve.

The one or more nerves can be a focus of the stimulation based on the placement, the geometric shape and/or the size of the microcoil 104. For example, the geometric shape and/or size of the microcoil 104 can be selected based on the intended focus of the stimulation and the placement can be selected based on the depth of the intended focus of the stimulation. In some instances, the microcoil 104 can include an elastic material. Accordingly, the microcoil 104 can be constructed using commonly available means. In some instances, the microcoil 104 can be printed on the elastic material using a three-dimensional printer. Three-dimensional printing can provide production and quality control advantages over current electrical stimulation leads. In other instances, the microcoil 104 can be wire wound from the elastic material. In some instances, the outermost layer of the microcoil 104 or the elastic material can be coated with a biologically compatible material to reduce the immune response and tissue encapsulation. Accordingly, the efficacy of the stimulation can remain about constant for the life of the system 10 of FIG. 1.

Generally, the microcoil 104 can be of a size less than or equal to 10 millimeters. In some instances, the microcoil 104 can be of a size less than or equal to 5 millimeters. In other instances, the microcoil 104 can be of a size less than or equal to 3 millimeters. In still other instances, the microcoil 104 can be of a size less than or equal to 1 millimeter. Because the microcoil 104 is of a small size and placed in close proximity to (or on the surface of) the epineurium of the peripheral nerve 102, it requires magnitudes less energy to generate the time-varying magnetic field 202 capable of activating the portion of the peripheral nerve than traditional magnetic stimulation.

In some instances, the size and/or geometric configuration of the microcoil 104 can focus the magnetic fields in different ways (e.g., to activate and/or suppress different portions of the peripheral nerve 102). For example, the geometric configuration can include the size of the microcoil, the orientation of the microcoil, the number of loops of the microcoil, and the shape of the microcoil. In some instances, a plurality of microcoils can increase the spatial selectivity of the stimulation compared to a single microcoil alone by reshaping the induced electric field to increase its spatial gradient along the direction of axons to increase the efficacy of the stimulation. Examples of potential different geometric configurations of the microcoil 104 or a plurality of microcoils that can activate the portion of the peripheral nerve 102 are schematically illustrated in FIGS. 3 and 4.

Figure 3:
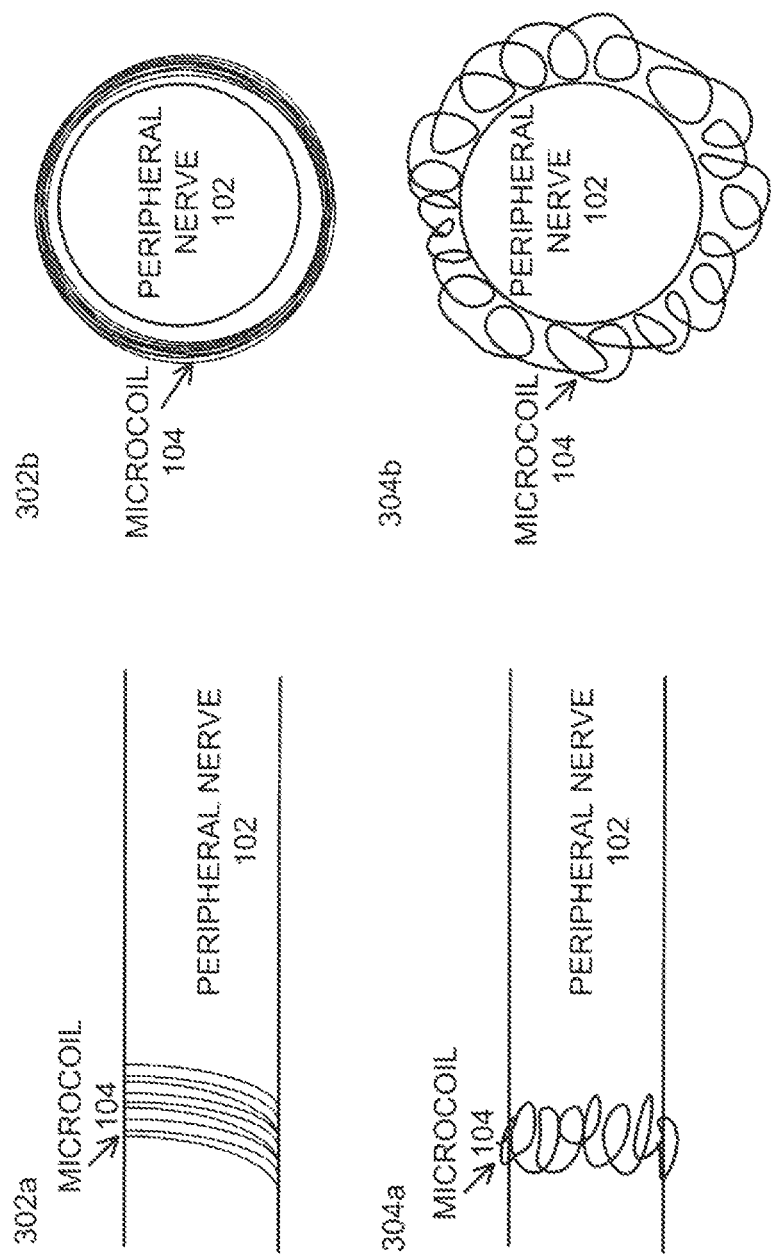
FIGS. 3 and 4 are schematic diagrams showing different geometric configurations of the microcoil in the system of FIG. 1.
Figure 4:
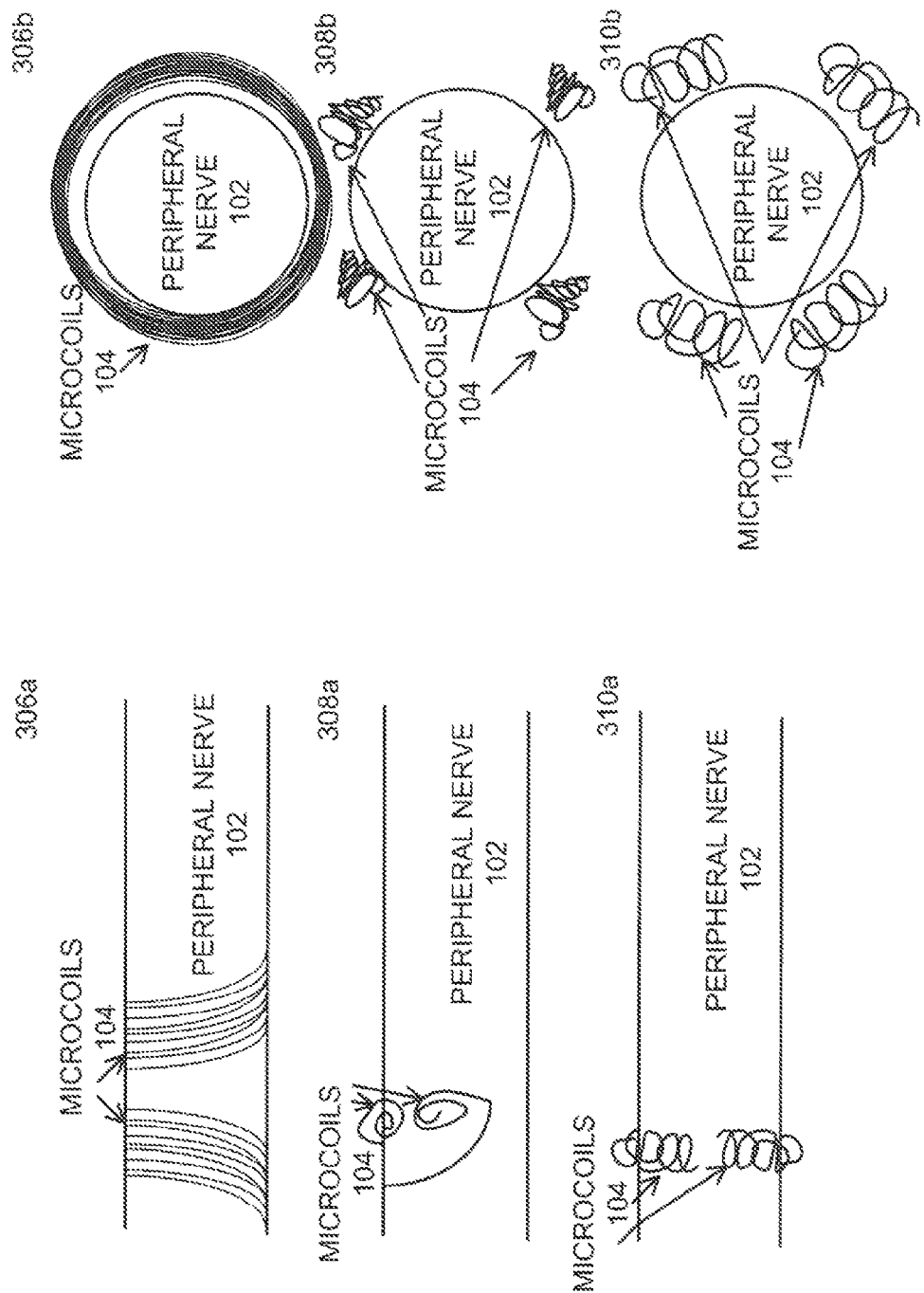

FIG. 3 illustrates examples of different geometric configurations of a single microcoil 104. The left column of FIG. 3 (302a, 304a) shows the microcoil 104 and the peripheral nerve 102 in the direction of the axons, and the right column of FIG. 3 (302b. 304b) shows the cross section of the nerve and the microcoil. One example, as shown in 302a and 302b, illustrates the microcoil 104 wrapping around a portion of the peripheral nerve 102 at an angle. Another example, as shown in 304a and 304b, illustrates the microcoil 104 wrapping around the peripheral nerve 102 with the direction of wire winding tangential to the direction of the peripheral nerve. The configuration of 304a and 304b can be expanded in the direction of the axons in the peripheral nerve 102 if the space is available.

Similar to bipolar or tripolar electrical stimulation, adding more coils in the direction of the axons in the peripheral nerve can reshape the induced electric field to increase its spatial gradient along the direction of the axons to increase the efficacy of the magnetic stimulation. FIG. 4 illustrates examples of different geometric configurations of a plurality of microcoils. The left column of FIG. 4 (306a, 308a, 310a) shows the microcoils 104 and the peripheral nerve 102 in the direction of the axons, and the right column of FIG. 4 (306b, 308b, 310b) shows the cross section of the nerve and the microcoil.

One example, as shown in 306a and 306b, illustrates the plurality of microcoils 104 wrapping around the peripheral nerve 102 at opposite angles. Another example, as shown in 308a and 308b, illustrates the microcoils 104 arranged similar to a mosquito coil, where the maximum magnetic field is under the center of the microcoils. In some instances, only a single coil can be shaped as the mosquito coil. However, more than one layer of microcoil 104 can be used to increase magnetic field density and corresponding induced electric field density. For example, the microcoils of 308a and 308b can be overlaid with overlap between the coils and separated by a thin insulator layer. The separation by the insulator layer can increase the magnetic field density and the induced electric field intensity.

A further example, as shown in 310a and 310b, illustrates the plurality of microcoils 104 wrapping around the nerve with the direction of wire winding tangential to the direction of the peripheral nerve 102. The plurality of microcoils 104 can increase spatial selectivity compared to a single microcoil. The configuration of 310a and 310b can be expanded in the direction of the axons if the space is available.

IV. Methods

Figure 5:
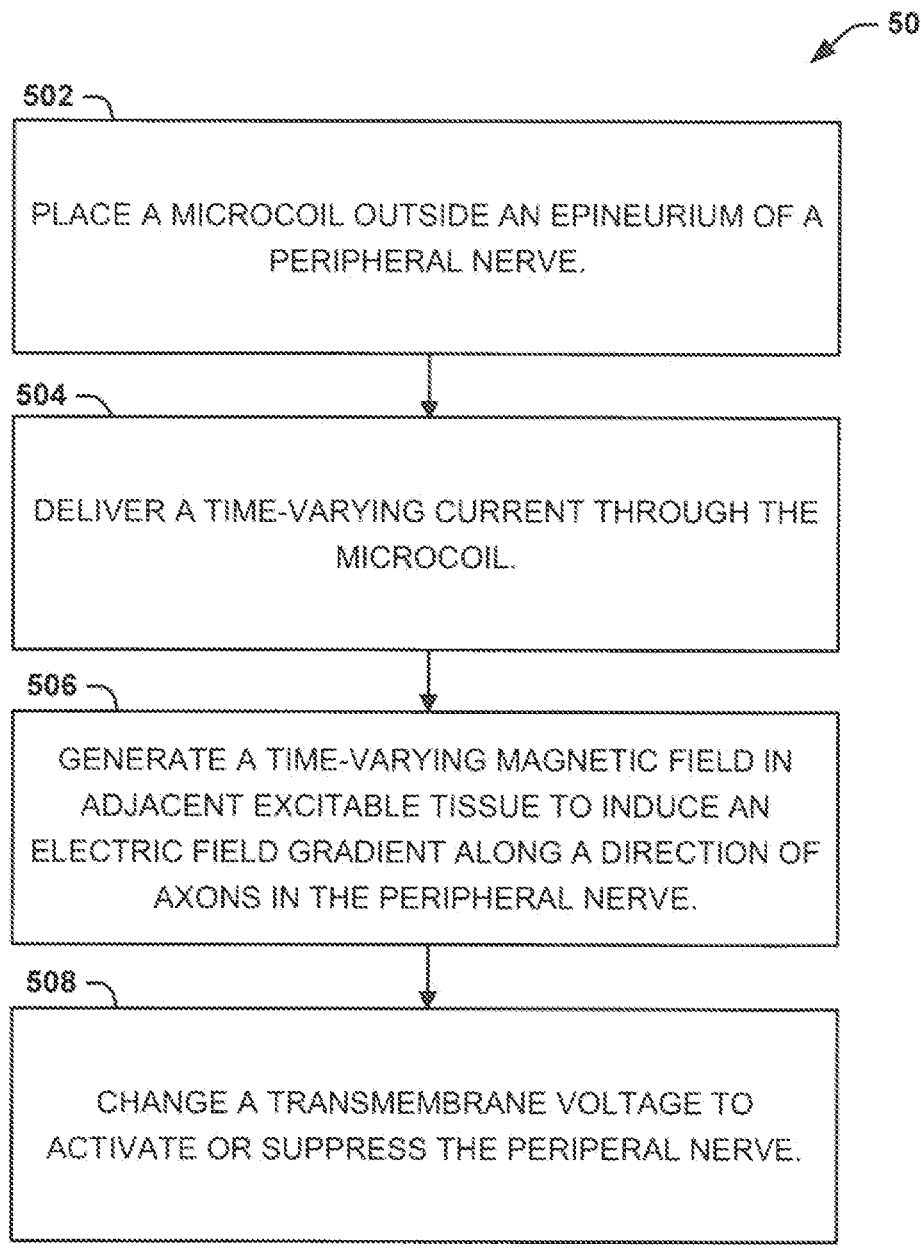
FIG. 5 is a process flow diagram illustrating a method for stimulating a peripheral nerve of a subject in accordance with another aspect of the present disclosure.

A second aspect of the present disclosure can include methods that can employ micromagnetic stimulation to stimulate a peripheral nerve. An example of a method 50 for stimulating a portion of a peripheral nerve of a subject is shown in FIG. 5. Another example of a method 60 for constructing a neural prosthetic device is shown in FIG. 6.

Figure 6:
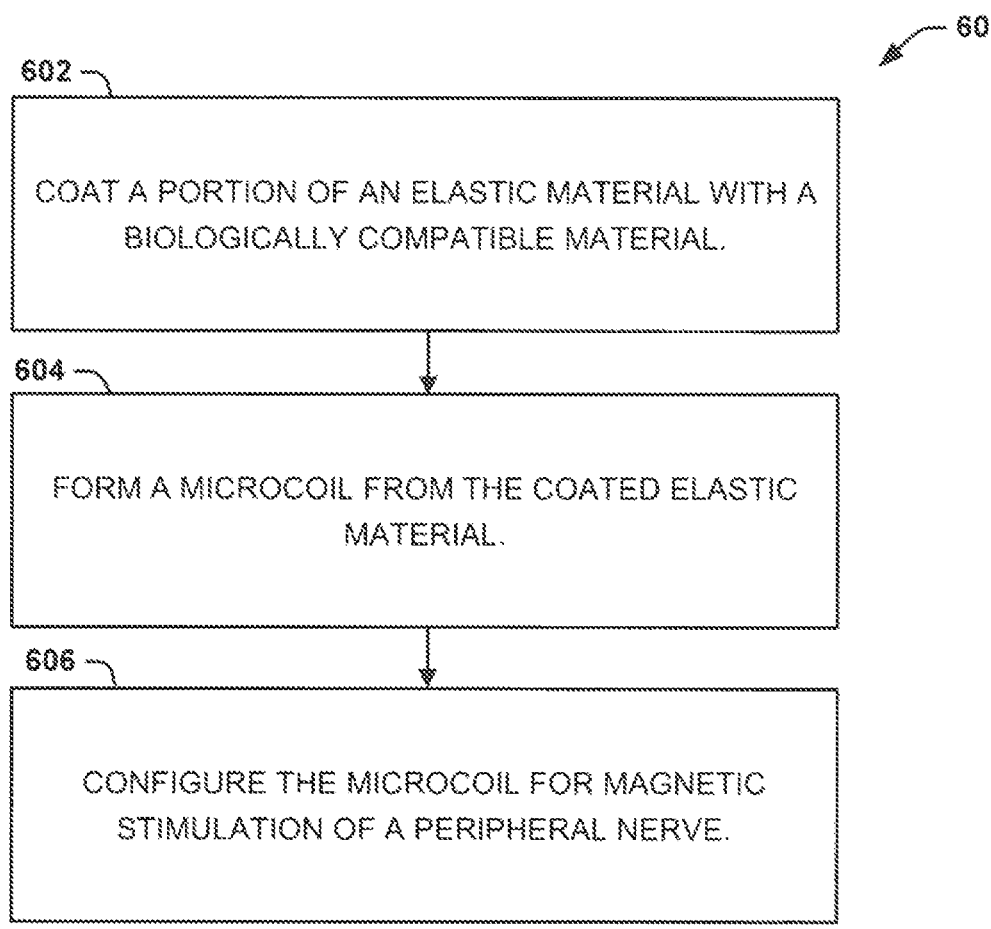
FIG. 6 is a process flow diagram illustrating a method for constructing a neural prosthetic device in accordance with another aspect of the present disclosure.

The methods 50 of FIG. 5 and 60 of FIG. 6 are illustrated as process flow diagrams with flowchart illustrations. For purposes of simplicity of explanation, the methods 50 of FIG. 5 and 60 of FIG. 6 are shown and described as executing serially, it is to be understood and appreciated that the present disclosure is not limited by the illustrated order, as some aspects could occur in different orders and/or concurrently with other aspects shown and described herein. Moreover, not all illustrated aspects may be required to implement method 50 or method 60.

Referring to FIG. 5, an aspect of the present disclosure can include a method 50 for stimulating a portion of a peripheral nerve of a subject. The stimulation can be micromagnetic stimulation of the portion of the peripheral nerve of the subject. The stimulation can be accomplished via a microcoil (e.g., microcoil 104) of a size of 10 millimeters or less that can be coupled to a stimulator device (e.g., stimulator 106). The stimulator device, in some instances, can be implemented by computer program instructions that are stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, some of the steps/acts can be implemented by a system comprising a processor that can access the computer-executable instructions that are stored in a non-transitory memory.

At 502, the microcoil can be placed outside of an epineurium, of the peripheral nerve. This can be done, for example, by a surgeon constructing a surgical procedure. However, this can be done with a device held outside the skin of a subject. In either case, the microcoil can be placed at a location outside the epineurium of the peripheral nerve in a position that facilitates the activation or suppression of the portion of the peripheral nerve. In some instances, the position can be chosen based on at least one of: a size of the microcoil, an orientation of the microcoil, a number of loops of the microcoil, and a shape of the microcoil.

In some instances, a plurality of microcoils can be placed outside the epineurium of the peripheral nerve. Each of the plurality of microcoils can be placed in a position that facilitates the activation or suppression of the portion of the peripheral nerve. In some instances, the plurality of microcoils can be overlaid with overlap between each of the microcoils, wherein each of the microcoils is separated by an insulator to increase the magnetic field density and the induced electric field intensity. The plurality of microcoils can increase the spatial selectivity of the stimulation compared to the single microcoil by reshaping the induced electric field to increase its spatial gradient along the direction of axons to increase the efficacy of the stimulation.

At 504, a time-varying current (e.g., generated by the stimulator 106) can be delivered through the microcoil (e.g., microcoil 104). At 506, a time-varying magnetic field can be generated by the microcoil to induce a current flow to activate the portion of the peripheral nerve. For example, the microcoil can produce the time-varying magnetic field in response to the time-varying current. At 508, a transmembrane voltage can be changed to activate of suppress the portion of the peripheral nerve. An electric field gradient based on the magnetic field can change the transmembrane voltage of the one or more axons sufficient to activate or suppress the portion of the peripheral nerve.

Referring now to FIG. 6, an aspect of the present disclosure can include a method 60 for constructing a neural prosthetic device (e.g., including microcoil 104 and stimulator 106) can stimulate a portion of a peripheral nerve of a subject. At 602, a portion of an elastic material can be coated with a biologically compatible material. The elastic material can be any biocompatible solid material that can deform and substantially return to its original shape and size after deformation forces have been removed. In some instances, the elastic material can be a metal. The biologically compatible coating can be applied to at least an outermost layer of the elastic material to reduce the immune response and tissue encapsulation that can decrease the efficacy of the stimulation over time.

At 604, the microcoil can be formed from the coated elastic material. In some instances, the microcoil can be printed on the coated elastic material using a three-dimensional printer. In other instances, the microcoil can be wire wound from the coated elastic material. The microcoil generally can be of a size less than or equal to 10 millimeters. In some instances, the microcoil can be of a size less than or equal to 5 millimeters. In other instances, the microcoil can be of a size less than or equal to 3 millimeters. In still other instances, the microcoil can be of a size less than or equal to 1 millimeter.

At 608, the microcoil provide magnetic stimulation to at least a portion of the peripheral nerve (e.g., according to the method 50 of FIG. 5). For example, the microcoil can be placed outside or in contact with the epineurium of the peripheral nerve. Indeed, the microcoil can provide the magnetic stimulation without penetrating the peripheral nerve. The microcoil can activate or suppress the portion of the peripheral nerve via electromagnetic induction.

From the above description, those skilled in the art will perceive improvements, changes and modifications. Such improvements, changes and modifications are within the skill of one in the art and are intended to be covered by the appended claims.

What is claimed is:

1. A system comprising:
a stimulator to provide a time-varying stimulus; and
a neural prosthesis operatively coupled to the stimulator and comprising at least one microcoil inductor,
wherein the at least one microcoil inductor comprises an elastic material coated with a biologically compatible material wound into a geometry selected to focus a magnetic field onto a peripheral nerve to generate an electric field gradient within the peripheral nerve to activate or suppress conduction in the peripheral nerve,
wherein the magnetic field is generated based on the time-varying stimulus, and
wherein the at least one microcoil inductor is configured to be wound into the geometry around the epineurium of the peripheral nerve.

2. The system of claim 1, wherein the time-varying stimulus comprises a time-varying current.

3. The system of claim 1, wherein the at least one microcoil inductor is of a size less than or equal to 10 millimeters.

4. The system of claim 1, wherein the at least one microcoil inductor is of a size less than or equal to 3 millimeters.

5. The system of claim 1, wherein the at least one microcoil inductor is of a size less than or equal to 1 millimeter.

6. The system of claim 1, wherein the neural prosthesis
delivers a time-varying current through the at least one microcoil inductor to generate a corresponding time-varying magnetic field in the peripheral nerve; and
induces an electric field gradient within an axon within the peripheral nerve based on the time-varying magnetic field to stimulate the peripheral nerve.

7. The system of claim 6, wherein the electric field gradient changes a transmembrane voltage of the axon sufficient to activate or suppress the peripheral nerve.

8. The system of claim 1, wherein the neural prosthesis further comprises a plurality of microcoil inductors each configured to wrap around the epineurium of the peripheral nerve in different geometries.

9. The system of claim 8, wherein the plurality of microcoil inductors increases a spatial selectivity of a stimulation with the magnetic field by reshaping the electric field gradient to increase an efficacy of the stimulation with the magnetic field.

10. The system of claim 8, wherein each of the microcoil inductors is separated by an insulator.

11. The system of claim 1, wherein a stimulation is based on at least one of: a size of the at least one microcoil inductor, an orientation of the at least one microcoil inductor, a number of loops of the at least one microcoil inductor, and a shape of the at least one microcoil inductor.

12. The system of claim 1, wherein the at least one microcoil inductor is configured to wrap around the epineurium of the peripheral nerve at an angle.

13. The system of claim 12, wherein the neural prosthesis further comprises at least two microcoil inductors configured to be wrapped around the epineurium of the peripheral nerve at opposite angles.

* * * * *